United States Patent

Adams et al.

[11] Patent Number: 5,864,239
[45] Date of Patent: Jan. 26, 1999

[54] APPARATUS FOR MEASURING A POWDER MASS FLOW

[75] Inventors: Horst Adams, Nonnenhorn, Germany; Kurt Seitz, Widnau, Switzerland

[73] Assignee: Wagner International, Alstatten, Switzerland

[21] Appl. No.: 808,307

[22] Filed: Feb. 28, 1997

[30] Foreign Application Priority Data

Dec. 3, 1996 [DE] Germany ................. 196 50 112.1

[51] Int. Cl.⁶ ............................................. G01R 27/04
[52] U.S. Cl. ................. 324/636; 73/30.03; 73/861.04; 73/861.08; 324/633
[58] Field of Search ........................ 324/633, 634; 73/861, 194; 250/358

[56] References Cited

U.S. PATENT DOCUMENTS

| | | | |
|---|---|---|---|
| 3,595,078 | 7/1971 | Beck | 73/194 |
| 3,635,082 | 1/1972 | Preilwitz et al. | 73/194 M |
| 4,509,366 | 4/1985 | Matsushita et al. | 73/861.02 |
| 4,603,257 | 7/1986 | Packer | 250/358 |
| 4,716,168 | 12/1987 | David | 73/861 |
| 4,743,143 | 5/1988 | Nagasaka | 406/14 |
| 4,807,480 | 2/1989 | O'Neill et al. | 73/861.04 |
| 5,389,883 | 2/1995 | Harper | 324/636 |
| 5,397,993 | 3/1995 | Tews | 324/634 |
| 5,546,006 | 8/1996 | Louge | 324/688 |
| 5,554,935 | 9/1996 | Krawszewski | 324/637 |

FOREIGN PATENT DOCUMENTS

| | | | |
|---|---|---|---|
| 0 297 309 A2 | 1/1989 | European Pat. Off. | B05B 12/08 |
| 44 06 046 A1 | 8/1995 | Germany | G01F 1/74 |
| A 3 125924 | 5/1991 | Japan | G01F 1/74 |
| 2 202 947 | 10/1988 | United Kingdom | G01N 22/00 |
| 2 271 637 | 4/1994 | United Kingdom | G01N 22/00 |

OTHER PUBLICATIONS

Japan Publication No. 58154622, Publication Date Sep. 14, 1983, Abstract.

*Primary Examiner*—Josie Ballato
*Assistant Examiner*—Thomas Valone
*Attorney, Agent, or Firm*—Fenwick & West LLP

[57] ABSTRACT

The instant invention relates to an apparatus for measuring a powder mass flow in a powder/gas mixture during the conveyance thereof through a feed pipe, the apparatus comprising a velocity measuring device for the powder/gas mixture, a mass measuring device for the powder mass per volume unit, and a calculating device to calculate the powder mass flow based on the velocity measured, the powder mass per volume unit measured, and the dimensions of the feed pipe. The mass measuring device comprises a microwave resonator and means for sensing the resonant frequency and/or the microwave amplitude of the microwave resonator. The microwave resonator is embodied by a coil which is applied on the outside of the feed pipe. The invention likewise proposes a method of measuring the powder mass flow in a feed pipe wherein measuring of the powder mass per volume unit involves establishing a reference resonance of a known powder mass flow, adjusting two measuring frequencies at either side of the reference resonance, measuring the resonator voltage at the adjusted measuring frequencies and forming the difference thereof for a powder mass flow to be measured, and determining the displacement of the resonant frequency based on the voltage differential.

3 Claims, 5 Drawing Sheets

APPARATUS FOR MEASURING A POWDER MASS FLOW

FIELD OF THE INVENTION

The instant invention relates to an apparatus for and a method of measuring a powder mass flow in a powder/air mixture while the powder/air mixture is being conveyed through a feed pipe.

BACKGROUND OF THE INVENTION

An apparatus of the kind in question which is described in DE-A-4 406 046 comprises a velocity measuring means for measuring the velocity of the powder/gas mixture in the feed pipe, a mass measuring means for measuring the powder mass per volume unit in a section of the feed pipe, the mass measuring means comprising a microwave resonator as well as means for detecting a change in the resonant frequency and/or the microwave amplitude of the microwave resonator and for deriving the powder mass in the feed pipe section from the resonant frequency and/or the microwave amplitude detected, and a calculating means for calculating the powder mass flow based on the velocity measured, the powder mass per volume unit measured, and the dimensions of the feed pipe. DE-A-4 406 046 likewise discloses a method of measuring a powder mass flow in a powder/gas mixture while the mixture is being conveyed through a feed pipe. With this method, the velocity of the powder/gas mixture is measured in the feed pipe, the powder mass per volume unit is measured in a section of the feed pipe by detecting a displacement of the resonant frequency in a microwave resonator disposed at the feed pipe, and the powder mass flow is calculated based on the velocity measured, the powder mass per volume unit measured, and previously known dimensions of the feed pipe.

The coating powder to be supplied to powder coating devices, in electrostatic coating systems, for example, is fluidized, i.e. the powder is intermixed with a gas, preferably with air in order to form a powder/air mixture which then is fed to the coating devices through feed pipes or tubes. In this context, it may become necessary to find out what quantity of powder per time unit actually is conveyed or delivered, in other words to determine the powder mass flow (g/min) during operation of the coating equipment, so as to be able to adjust the powder mass flow to a desired value or to maintain an set value.

In known powder coating equipment, the air pressure used to supply powder by means of injectors or venturi nozzles has been measured with the aid of pressure gauges providing values in bar, or the air quantities required for such supply have been determined in m$^3$/h.

However, measurements of the air pressures and air quantities offer no more than an indirect and unreliable indication of the actual output of powder. For instance, when a powder reservoir is empty, supply pressures or air quantities continue to be indicated although powder can no longer be delivered.

The above mentioned DE-A-4 406 046 suggests that two parameters be measured to determine the powder mass flow, namely:

the velocity V of the powder/air mixture in the feed pipe in m/sec and the powder mass per volume unit $M_V$ in the feed pipe in g/cm$^3$.

Based on these two parameters V and $M_V$, in combination with the dimensions of the feed pipe which are assumed to be known, especially the cross section Q of the feed pipe, the resulting powder mass flow fed and delivered, i.e. the powder quantity per time unit $M_T$ in g/min is given as follows:

$$M_T[g/min]=V[m/sec]*M_V[g/cm^3]*Q[cm^2]*6000.$$

According to the publication cited above the velocity is measured by means of two spaced apart measuring electrodes which sense charge fluctuations at the feed pipe generated by the powder/gas mixture being conveyed. The powder mass per volume unit is measured by means of a microwave resonator which senses variations of the dielectric constant and/or the microwave absorption in a resonant volume of the feed pipe by way of a shift or displacement of the resonant frequency or a change of the microwave amplitude in the resonator.

EP-A-297 309 discloses a method of and an apparatus for measuring and controlling the amount of powder in a powder coating system. Here powder quantities supplied per unit time to a spray coating machine are measured. The method provides for measuring the density of the powder in the powder/gas flow by a beam measuring device. The gas quantity per unit time is determined, and the amount of powder conveyed per unit time is established on the basis of the following equation c=a·b.

U.S. Pat. No. 4,807,480 describes a method of measuring the flow rate of an powder/air mixture in which the flow velocity of the mixture is detected by sensors which are spaced from each other and which sense charge fluctuations in the powder/air mixture. To accomplish this, a corona needle electrode injects a charge into the powder/air mixture and the sensors detect the charge.

JP-A-3-125924 discloses a flowmeter for a powder flow. Here, a tracer material is introduced into a stream of powder and two sets of microwave transmitters and receivers are used to detect the powder mass flow.

SUMMARY OF THE INVENTION

It is an object of the invention to provide an apparatus and a method by which the powder mass flow conveyed in a powder coating system during operation thereof and the powder quantity output can be measured more accurately and with less susceptibility to disturbance than in the prior art.

The invention provides an apparatus for measuring a powder mass flow in a powder/gas mixture while the powder/gas mixture is being conveyed through a feed pipe, comprising the following features: a velocity measuring means to measure the velocity of the powder/gas mixture in the feed pipe; a mass measuring means to measure the powder mass per volume unit in a section of the feed pipe, this means comprising a microwave resonator as well as means for detecting the resonant frequency and/or the microwave amplitude of the microwave resonator and deriving the powder mass in the resonant volume from the resonant frequency and/or the microwave amplitude detected; and a calculating means to calculate the powder mass flow based on the velocity measured, the powder mass per volume unit measured, and the dimensions of the feed pipe.

In accordance with a first aspect of the invention the microwave resonator is of helical shape. In principle, it is a coil which is formed on the outside of the electrically non-conductive feed pipe.

High frequency a.c. voltage (in the microwave range) causes this coil to resonate. Performing the resonance measurement by a helix resonator rather than, for instance, a cavity resonator, as used in the prior art, has the advantage that first the structural dimensions are much smaller so that the sensor can be integrated directly in the spray gun of a powder coating apparatus. Furthermore, particularly acute resonance can be generated by a helical resonator and, therefore, better quality is obtained. These two effects in combination offer greater accuracy and sensitivity in measuring the powder density or the powder mass per volume unit.

According to a particularly advantageous embodiment of the invention the coil of the helix resonator is not simply a wire wound around the feed pipe. Instead, it is a metal layer formed on the outside of the feed pipe by a vapor deposition process. Vapor deposition of a metallic thin film permits a helical or coil structure to be formed of very little coil material and, therefore, an inexpensive helix resonator is obtainable even when gold is used as the coil material. Among the precious metals, gold has the best corrosion resistance and lends itself to very accurate processing by etching or masking techniques so that a very precise helix resonator of extremely high quality can be formed which, in turn, provides optimum measuring sensitivity.

According to another aspect of the invention a method is provided of measuring a powder mass flow in a powder/gas mixture while the powder/gas mixture is being conveyed through a feed pipe, wherein the velocity of the powder/gas mixture in the feed pipe is measured; the powder mass per volume unit in a section of the feed pipe is measured by detecting a resonant frequency shift in a microwave resonator disposed at the feed pipe; and the powder mass flow is calculated based on the velocity measured, the powder mass per volume unit measured, and the previously known dimensions of the feed pipe. Measuring the powder mass per volume unit involves determining a reference resonance for a known reference powder mass flow, setting two measuring frequencies at either side of the reference resonance, measuring the resonator voltages at the set measuring frequencies for a powder mass flow to be measured and deriving a difference between them, and then determining the displacement of the resonant frequency on the basis of the voltage difference.

It was known in the art, especially from DE-A-4 406 046 to evaluate the displacement of the resonant frequency as a measure of the powder density in the pipe. Yet it was not disclosed how that should be done. The instant invention, therefore, suggests a specific method of measuring the frequency shift with respect to a reference resonant frequency. This new method in particular has the advantage that an absolute frequency measurement need not be made at any time.

More specifically, the method according to the invention makes use of electronics by which, to begin with, a rather broad frequency range is scanned at a known reference powder mass flow, for example when the feed pipe is empty, and a resonance, i.e. a voltage peak is looked for in this range. When this resonance has been found, the electronic means measures the voltage $U_{max}$ at the maximum of the resonance and sets two marks or measuring frequencies symmetrically with respect to the maximum. In a particular embodiment these marks may be set, for instance, at approximately one half $U_{1/2}$ of the maximum amplitude of the resonance, to the right and left of the maximum. In this context, neither the absolute frequency $v_0$ of the resonance nor the absolute height $U_{max}$ of the voltage maximum have to be considered. What is important is that the amplitude values are the same at the left and right sides of the maximum.

When the dielectric constant in the resonator varies, e.g. by introduction of powder into the feed pipe, the resonance curve becomes displaced with respect to the two previously set marks. That means, the amplitude value at one frequency mark rises, while that at the other drops. Now, measurement of the difference between the two voltage values will show that the voltage difference is zero for the reference powder mass flow, and that within a wide range it is proportional to the resonant frequency displacement with regard to any other powder mass flow. The density of the powder mass flow in the feed pipe can be derived, in a manner known to the skilled person, from the displacement of the resonant frequency.

In addition to the fact that the novel method requires no highly accurate measurement of the absolute frequency, it has yet another advantage. During spray intervals, in other words when there is no powder in the feed pipe and none flows through the resonator, automatic zero balancing may be performed. This means that the two frequency marks are reset by the electronics to be symmetrical once more to the maximum amplitude. In this manner shifts in frequency due to external influences, such as temperature and moisture may be compensated.

Of course, it is possible to combine the apparatus and the method according to the invention.

BRIEF DESCRIPTION OF THE DRAWINGS

The invention will be described further, by way of example, with reference to the accompanying drawings, in which.

DESCRIPTION OF PREFERRED EMBODIMENTS

Figure 1A:
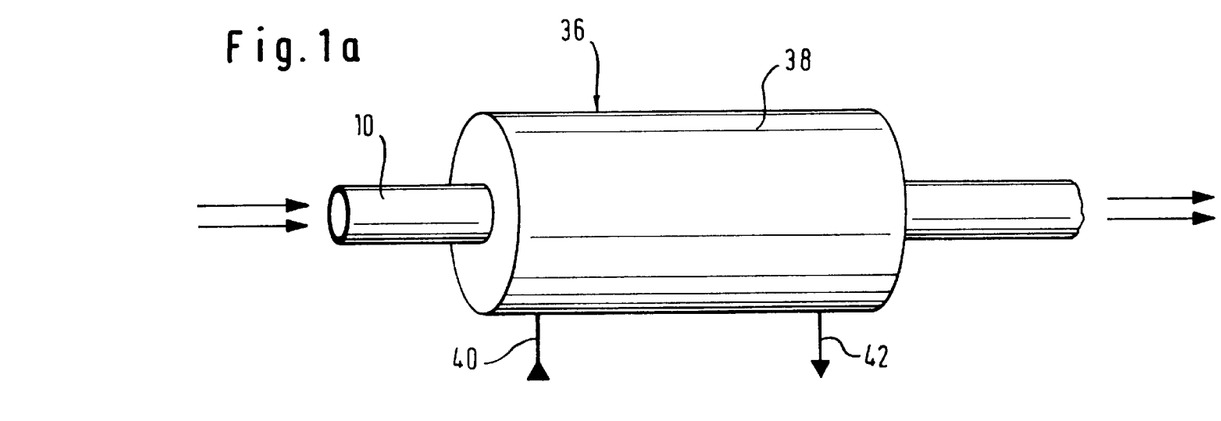
FIGS. 1a and 1b are an overall view and a schematic partially sectional view, respectively, of an embodiment of a microwave resonator according to the invention.
Figure 1B:
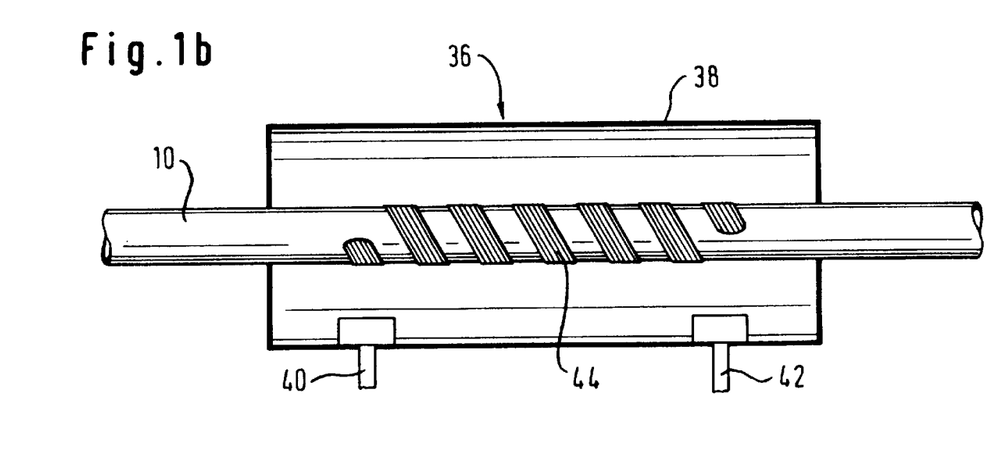

FIGS. 1a and 1b show an embodiment of a microwave resonator 36 of the mass measuring means used to determine the powder quantity per volume unit in a feed pipe 10.

The feed pipe 10 is a pipe or tube made of ceramics or glass; it may also be embodied by a plastic hose or any other conduit suitable for conveying material in coating equipment. The feed pipe 10 is electrically non-conductive. The powder/gas flow passes the feed pipe 10 in the direction of the arrows shown in FIG. 1.

The resonator 36 is shielded against interference fields by a metal cylinder 38 which surrounds the resonator member 44 proper. The metal cylinder 38 has a high frequency input terminal 40 and a high frequency output terminal 42 for coupling in microwaves and tapping the resonator voltage, respectively.

As indicated in FIG. 1b, coaxial cables may be connected to the input and output terminals 40 and 42 so as to link the microwave resonator with a microwave source and a voltage sensor, respectively, as will be described in greater detail below with reference to FIG. 3.

The resonator member 44, in the form of a helix or coil surrounding the feed pipe 10, is located within the shielding metal cylinder 38. The microwave resonator according to the invention may be embodied by a wire coil 44 wound around the feed pipe 10. Such a resonator requires very little space so that it may be integrated directly into the spray device, e.g. the spray gun of coating equipment. Moreover, a precisely defined resonance can be achieved with a helical resonator and, as a consequence, high quality is assured. Therefore, the sensitivity is increased in measuring the powder density.

According to a particularly preferred embodiment of the invention the helix resonator is applied as a thin film metal layer 44 on the feed pipe 10, especially by vapor deposition. The helical configuration is defined by etching or masking techniques. The preferred coil material to be used is gold because it is highly resistant to corrosion and convenient to process. In view of the fact that vapor deposition of a thin film can be accomplished with only very little material for the helical layer 44, an inexpensive microwave resonator can be obtained even if gold is used as the coil material. The well defined shape of the helix from thin film gold material provides further improvement of the coil quality and optimum measuring sensitivity.

The principles of mass measurement by means of the microwave resonator 36 are as follows:

Part of the microwave field generated by the resonator penetrates the wall of the feed pipe 10 thus entering the powder/air mixture. What is measured is the resonant frequency $v_0$ of the resonator or its quality Q. These values depend on the following characteristics of the medium in the resonant area:

the dielectric constant and the absorption (loss factor).

Figure 2A:
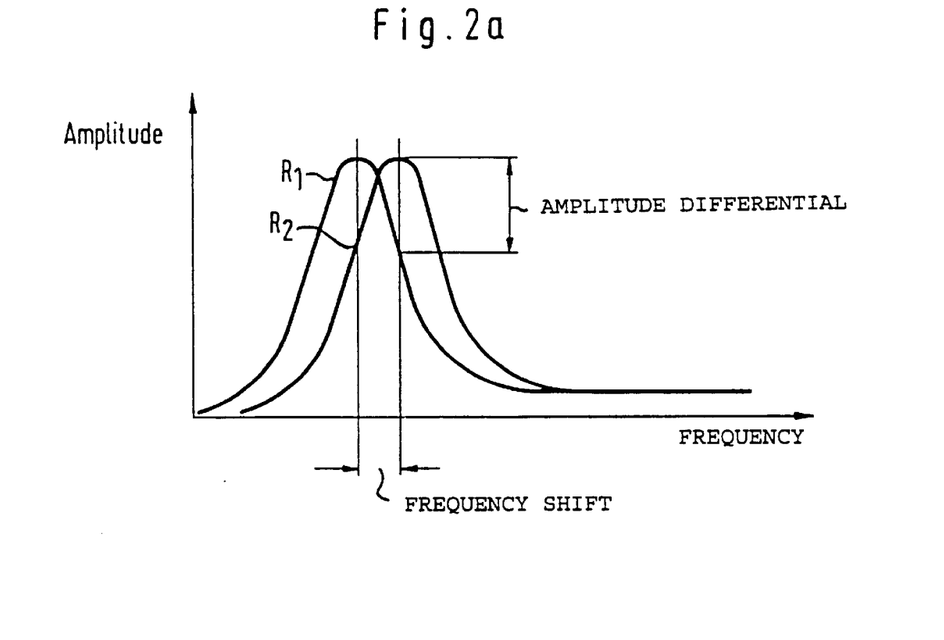
FIGS. 2a, 2b, 2c are graphs illustrating the signals generated by the microwave resonator.

Variations of the dielectric constant and absorption are proportional to variations of the powder quantity in the resonant area or resonant volume which comprises a certain section of the feed pipe 10. Consequently, a change in the amount of powder, i.e. powder mass within the resonant volume, produces a shift or displacement of the resonant frequency as well as a hange of the quality and thus of the microwave amplitude. FIG. 2a presents two resonance curves $R_1$, $R_2$ for different powder quantities in the resonant volume. This fig. merely illustrates the frequency displacement between the two curves $R_1$ and $R_2$, it does not show the change in microwave amplitude due to the change in quality. The quality of the microwave resonator decreases as the powder quantity increases so that, in fact, curve $R_2$ takes a flatter course than curve $R_1$ and has a lower amplitude. The amplitude differential is indicated in FIG. 2a.

Variations of the powder quantity in the resonant volume can be determined in the form of relative mass measurements by measuring the resonant frequency shift or the microwave amplitude change for different amounts of powder within the resonant volume. An absolute determination of the mass can be made by calibrating the microwave resonator to a reference resonant frequency and a reference microwave amplitude for a predetermined known powder quantity. A shift of the resonant frequency or a change of the microwave amplitude with respect to the reference frequency or reference amplitude, respectively, then is a measure of the powder quantity present in the resonant volume as compared to the predetermined known powder quantity. Thus the absolute powder quantity per volume unit can be determined in suitable evaluating means on the basis of the resonant frequency shift or the microwave amplitude variation, or the change in quality Q, as against the reference values.

The method according to the invention for measuring the powder mass flow and, more specifically, the shift of the resonant frequency will be explained below with reference to FIGS. 2b and 2c.

Figure 2B:
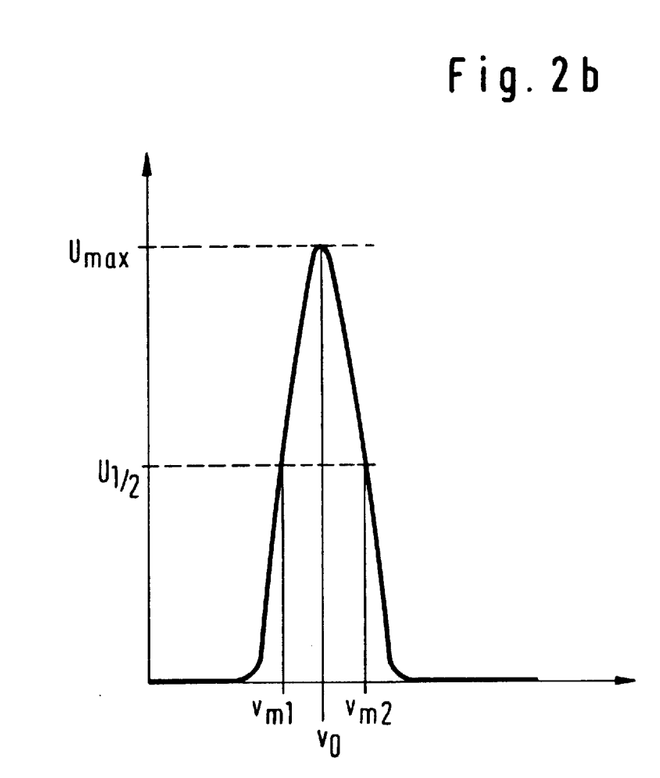

FIG. 2b shows the resonant curve of the helical microwave resonator 36 of FIGS. 1a and 1b, having a voltage maximum $U_{max}$ at frequency $v_0$. In the case of FIG. 2b the feed pipe is empty, i.e. the powder mass flow is zero.

With the method according to the invention, electronic means first scan a preset broad frequency range, while the feed pipe is empty, looking for a resonance in this range, i.e. a voltage peak. As soon as this resonance or voltage peak has been located the voltage at the maximum $U_{max}$ occurring at the resonant frequency $v_0$ is measured. Subsequently two marks or measuring frequencies, for example $v_{m1}$ and $v_{m2}$, are set at either side of the resonant frequency $v_0$. These measuring frequencies are arranged symmetrically with respect to the maximum amplitude. In the case of FIG. 2b, the measuring frequencies are set approximately at one half $U_{1/2}$ of the maximum amplitude of the resonance, to the right and left of the maximum. The absolute frequency $v_0$ of the resonant voltage and the absolute voltage maximum $U_{max}$ of the resonance (signal amplitude) are not decisive in this context. The only thing to be made sure is that the amplitude values, at $v_{m1}$ and $v_{m2}$, at the left and right sides of the maximum are identical. The example chosen of half the maximum resonant amplitude to fix the measuring frequencies $v_{m1}$ and $v_{m2}$ has the advantage that the relationship between the voltage differential and the resonant displacement is approximately linear at these measuring points. However, the essential feature of the invention is that the measuring frequencies to the left and right of the maximum are set to be symmetrical with respect to $U_{max}$.

Figure 2C:
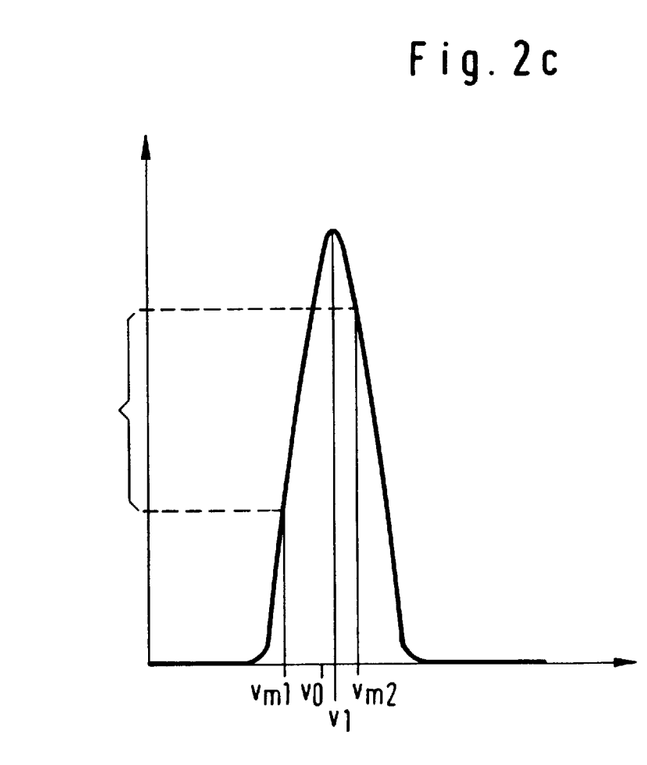

When the dielectric constant in the microwave resonator changes, such as by the entry of powder into the feed pipe, the resonant frequency shifts with respect to the reference resonant frequency, e.g. to $v_1$ as indicated in FIG. 2c. The electronic means now senses the voltage amplitudes of the new resonator voltage at measuring frequencies $v_{m1}$ and $v_{m2}$ and, as shown in FIG. 2c, a considerable difference in voltage between the two measuring frequencies is observed; in other words the amplitude value pertaining to the one frequency mark $v_{m2}$ rises while the other one of frequency mark $v_{m1}$ drops. If the difference is measured between the voltage values at the two frequency marks in question, with an empty feed pipe or for the reference powder mass flow, the result will be zero voltage difference. For all other powder mass flows, the differential voltage will be essentially proportional to the displacement of the resonant frequency, within a wide frequency range. As explained above, the powder density in the feed pipe can be established on the basis of the resonant frequency shift.

Figure 3:
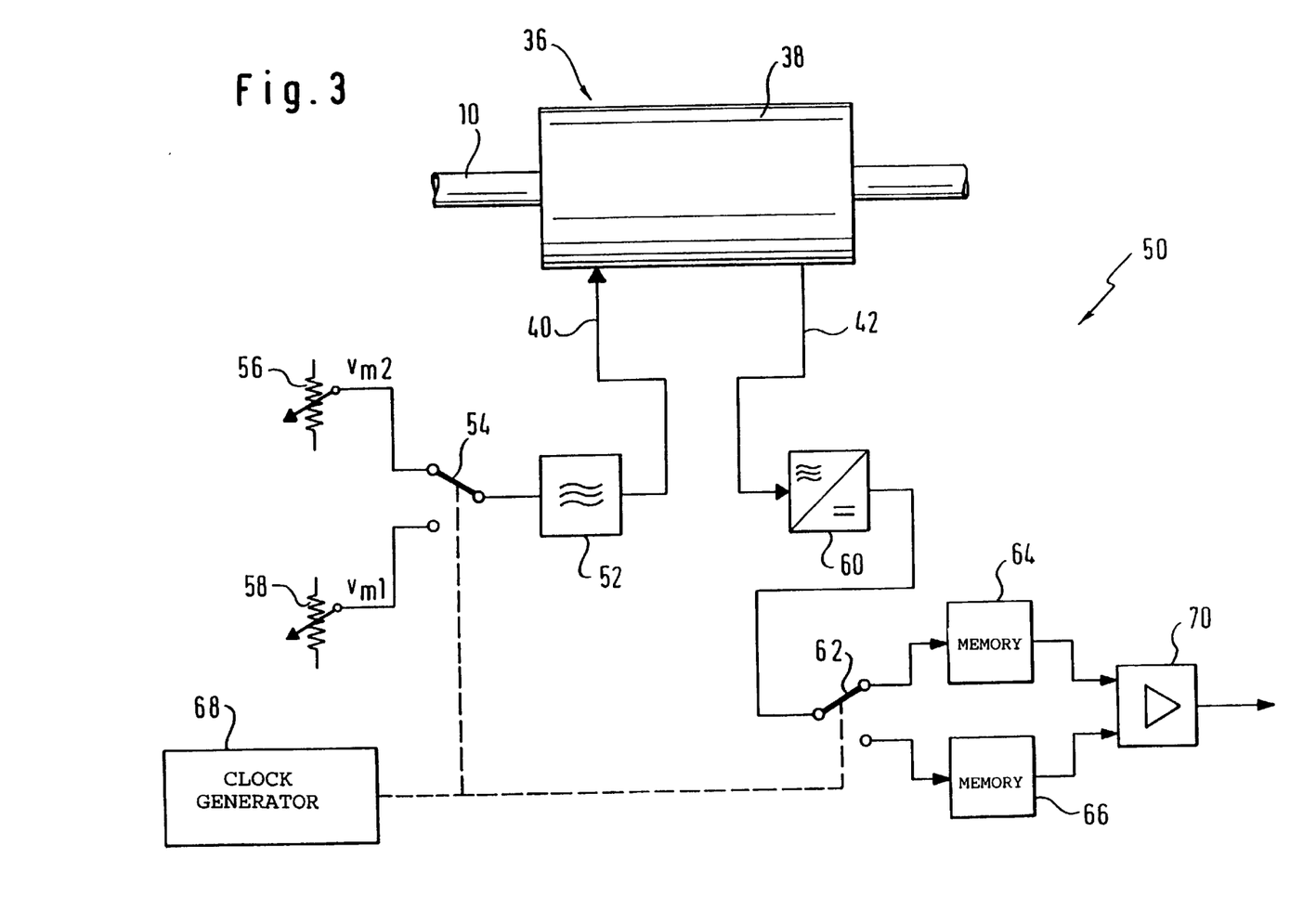
FIG. 3 is a schematic illustration of electronics used to carry out the method of the invention.

In FIG. 3, an electronic circuit, or electronics, for carrying out the measurement of the powder mass flow according to the invention is designated in general by 50. The high frequency input terminal 40 of the microwave resonator 36 is coupled to an adjustable high frequency oscillator 52 adapted to be switched by means of a switch 54 between the upper measuring frequency $v_{m2}$ and the lower measuring frequency $v_{m1}$. These two measuring frequencies are adjustable by way of potentiometers 56 and 58, respectively. As explained above, they are fixed beforehand on the basis of the reference powder mass flow. The microwave resonator 36 through which the powder mass flow to be measured passes thus may be excited by the high frequency oscillator 52 at one of the two measuring frequencies set.

Upon excitation of the microwave resonator 36 at the measuring frequencies $v_{m1}$ and $v_{m2}$, corresponding resonator voltages will be available at the high frequency output terminal 42 for supply to a rectifier 60. A switch 62 selectively passes these voltages to a memory 64 for the higher measuring frequency $v_{m2}$ or a memory 66 for the lower measuring frequency $v_{m1}$. The switches 54 and 62 are switched in synchronism by a clock generator 68 so that excitation of the microwave resonator 36 at the lower measuring frequency $v_{m1}$ will cause the output voltage of the resonator 36 to be applied to the "lower" memory 66, whereas excitation of the microwave resonator 36 at the higher measuring frequency $v_{m2}$ will cause the output voltage of the resonator to be applied to the "upper" memory 64. The voltage values memorized are applied to a differential amplifier 70 whose output signal is passed on to a processing unit (not shown) for further processing in accordance with the method described above so that the displacement of the resonant frequency of the microwave resonator 36 with respect to the reference resonance may be determined on the basis of the voltage difference and, based on the latter, the powder density in the measuring area of the feed pipe 10 may be established.

The method according to the invention has the great advantage of not requiring a highly accurate measurement of the absolute resonant frequencies of a known reference powder mass flow and of a powder mass flow to be determined. Furthermore, automatic zero balancing may be performed during spraying intervals when there is no powder in the feed pipe or, for that matter, in the resonator. This means that the electronics will readjust the two measuring frequencies to be symmetrical to the maximum amplitude of the resonance. In this manner frequency shifts may be compensated which are caused by environmental influences, such as temperature and humidity variations. The method preferably is carried out with the aid of the helical resonator specified above.

Figure 4:
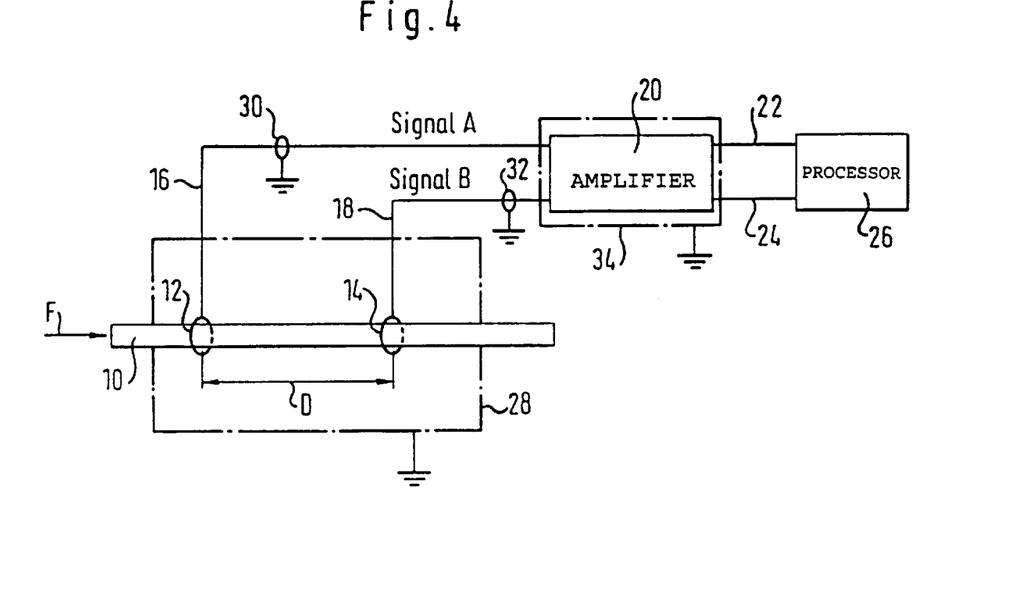
FIG. 4 is a schematic illustration of the velocity measuring means of the apparatus according to the invention.

FIG. 4 is a diagrammatic presentation showing the structure of a flow velocity measuring means. Two measuring electrodes 12, 14 are provided at a given spacing D on the feed pipe 10. They are connected by signal lines 16, 18 to an amplifier 20. The outputs 22, 24 of the amplifier 20 are connected to a measured value processing means 26, for example an X(t) recorder. In the case of the embodiment illustrated in FIG. 4, the two measuring electrodes 12, 14 are provided in the form of copper rings placed around the feed pipe 10.

A grounded shielding 28 surrounds the portion of the feed pipe 10 where the measuring arrangement including the measuring electrodes 12, 14 is positioned. Also the signal lines 16, 18 and the amplifier comprise shieldings 30, 32, and 34, respectively. The amplifier 20 of the embodiment shown is a sensitive test amplifier.

Figure 5:
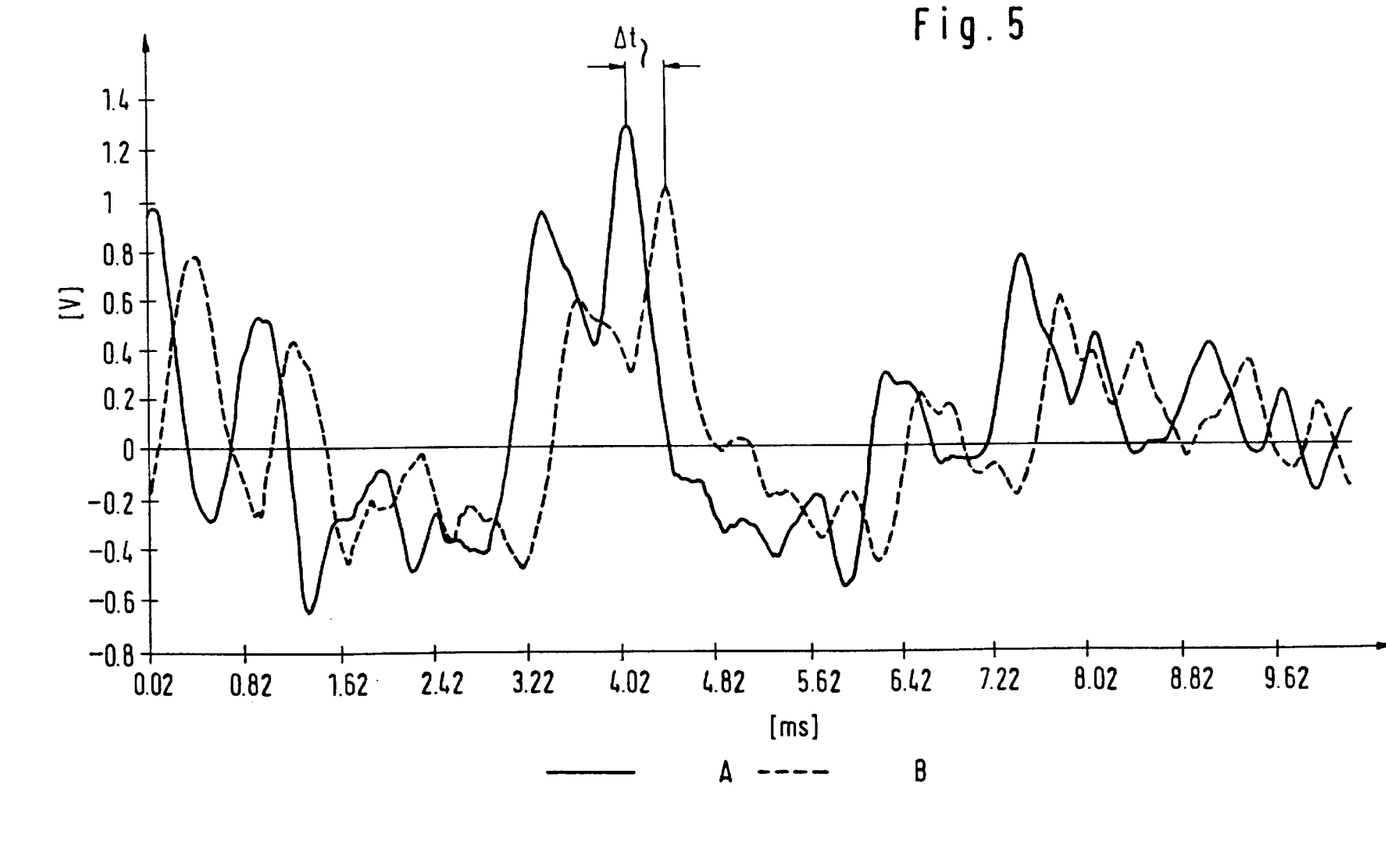
FIG. 5 is a graph illustrating signals A and B plotted versus time, as detected by the velocity measuring means shown in FIG. 4.

The flow velocity measuring means operates as follows: Powder particles of the powder/air mixture being conveyed through the feed pipe 10 in the direction of arrow F become charged electrostatically by friction with the material of the plastic hose. These charges influence, i.e. induce voltages in the two measuring electrodes 12, 14 disposed at a suitable spacing D on the plastic hose, and these voltages are applied to the sensitive test amplifier 20 via the shielded signal lines 16, 18. The amplifier measures and amplifies the influence voltages generated by the charged powder particles at the locations of the two electrodes. The signals measured, signal A from measuring electrode 12 and signal B from measuring electrode 14, are illustrated in FIG. 5. The temporal course of the two signals matches by approximately 97% (correlation). The amplifier 20 passes the amplified signals A, B to the measured value processing means 26 which displays the signal responses on the X(t) recorder and evaluates them. As the signal responses are largely in agreement, the time intervals between two respective signal peaks can be determined unambiguously and, therefore, the velocity V of the powder particles in the powder/air mixture being conveyed through the feed pipe 10 can be calculated on the basis of the temporal shift or the temporal offset $\Delta t$ between the signal peaks and the known spacing D between the measuring electrodes: $V = D/\Delta t$.

In a modified embodiment of the measuring means the air used to convey the particles is caused to pulsate so that the two measuring electrodes at the plastic hose sense pulsating influence voltages. Instead of the rather random voltage variations illustrated in FIG. 5, this will result in essentially periodic signal responses in dependence on the pulse frequency, having only a minor superimposed ratio of noise. The velocity V of the powder particles can be established, as described above, on the basis of the period in time between two corresponding signals peaks and the known spacing D between the measuring electrodes 12, 14. This modified embodiment of the measuring apparatus and method has the advantage that the test amplifier 20 may be tuned within a narrow band to the modulation frequency whereby an improvement of the signal to noise ratio is obtained.

In another variant embodiment additional phase sensitive evidence of the pulsating charges may be given by means of a lock-in amplifier. In this event the signals, on the one hand, are subjected to frequency selective amplification, tuned within a narrow band to the modulation frequency. On the other hand, the lock-in amplifier may be set or "locked" to a fixed phase with respect to the excitation pulse. This fixed phase may be determined on the basis of the known dimensions of the flow velocity/rate measuring means. This provides further improvement of the signal to noise ratio.

Based on the measured velocity of the powder/air mixture V, the measured powder mass per volume unit $M_V$, and the cross section Q of the feed pipe 10, a calculating means (not shown) may then calculate, by multiplication, the powder mass flow in the feed pipe, i.e. the powder quantity conveyed per time unit.

The features of the invention disclosed in the above specification, in the drawings, and claims may be significant both individually and in any combination thereof to realize the invention in its various embodiments.

What is claimed is:

1. An apparatus for measuring a powder particle mass flow in a powder particle/gas mixture while the powder particle/gas mixture is being conveyed through a feed pipe, comprising:

a velocity measuring means to measure the velocity of the powder particle/gas mixture in the feed pipe, a mass measuring means to measure the powder particle mass per volume unit in a section of the feed pipe, and comprising a high frequency resonator including a coil formed on the outside of the feed pipe including a layer of vapor deposited precious metal in the form of a thin film helix, and also comprising means for detecting a change in one of resonant frequency and high frequency amplitude of the high frequency resonator to indicate the powder particle mass per volume unit in the feed pipe section from the detected one of the resonant frequency and high frequency amplitude, and a calculating means to calculate the powder particle mass flow based on the velocity measured, the powder particle mass per volume unit measured, and the dimensions of the feed pipe.

2. An apparatus for measuring a powder particle mass flow in a powder particle/gas mixture while the powder particle/gas mixture is being conveyed through a feed pipe, comprising:

a velocity measuring module disposed with respect to the feed pipe for providing an indication of velocity of the powder particle/gas mixture in the feed pipe, a mass measuring module disposed with respect to a section of the feed pipe and including a high frequency resonator comprising a coil positioned on the outside of the section of feed pipe in the form of a thin film helix for responding to powder particle mass per volume unit in the section of the feed pipe, the mass measuring module also including a detector of change in a selected operating electrical parameter of the high frequency resonator for providing therefrom an indication of powder particle mass per volume unit detected in the section of the feed pipe, and a calculating module coupled to respond to the indication of velocity, and the powder particle mass per volume unit measured, and the dimensions of the feed pipe to provide an output indication of powder particle mass flow in the feed pipe.

3. The apparatus as claimed in claim 2, wherein the thin film helix includes a layer of vapor deposited precious metal.

* * * * *